United States Patent [19]

Hall

[11] Patent Number: 4,749,715

[45] Date of Patent: Jun. 7, 1988

[54] 7-OXABICYCLOHEPTANE SUBSTITUTED AMINO PROSTAGLANDIN ANALOGS

[75] Inventor: Steven E. Hall, Ewing Township, Mercer County, N.J.

[73] Assignee: E. R. Squibb & Sons, Inc., Princeton, N.J.

[21] Appl. No.: 20,640

[22] Filed: Mar. 2, 1987

[51] Int. Cl.$^4$ .................... A61K 31/34; C07D 307/00; C07D 405/08
[52] U.S. Cl. .................................. 514/382; 514/469; 548/253; 549/469
[58] Field of Search ................ 549/463; 514/469, 382; 548/253

[56] References Cited

U.S. PATENT DOCUMENTS

| | | | |
|---|---|---|---|
| 3,980,691 | 7/1976 | Schneider | 560/121 |
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 549/463 |
| 4,456,615 | 6/1984 | Nakane et al. | 424/285 |
| 4,456,617 | 6/1984 | Nakane et al. | 424/285 |
| 4,607,048 | 8/1986 | Nakane | 514/469 |
| 4,638,012 | 1/1987 | Nakane et al. | 549/463 |
| 4,639,461 | 1/1987 | Nakane | 514/382 |

FOREIGN PATENT DOCUMENTS

| | | |
|---|---|---|
| 0043292 | 8/1982 | European Pat. Off. |
| 0082646 | 6/1983 | European Pat. Off. |
| 2039909 | 8/1980 | United Kingdom |

Primary Examiner—Robert Gerstl
Attorney, Agent, or Firm—Lawrence S. Levinson; Burton Rodney

[57] ABSTRACT

7-Oxabicycloheptane substituted amino prostaglandin analogs are provided having the structural formula

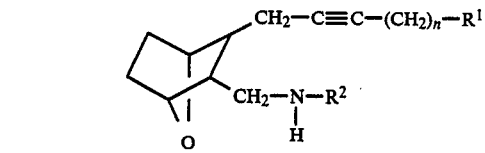

wherein n is 1 to 5; $R^1$ is $CO_2H$, $CO_2$ lower alkyl or

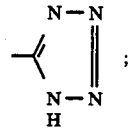

and $R^2$ is

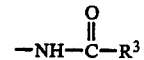

wherein $R^3$ is lower alkyl, aralkyl, —NHalkyl or —N-Haryl, or $R^2$ is

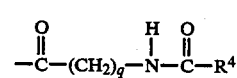

wherein q is 1 to 12, and $R^4$ is lower alkyl, lower alkenyl, lower alkynyl, aryl, arylalkyl, lower alkoxy, aryloxy, arylalkyloxy, amino, alkylamino arylamino, arylalkylamino, lower alkyl-S—, aryl-S—, arylalkyl-S—,

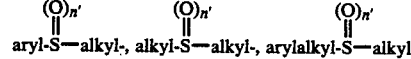

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease and are useful in the preparation of radiolabelled analogs.

16 Claims, No Drawings

7-OXABICYCLOHEPTANE SUBSTITUTED AMINO PROSTAGLANDIN ANALOGS

DESCRIPTION OF THE INVENTION

The present invention relates to 7-oxabicycloheptane substituted amino prostaglandin analogs which include an acetylenic moiety in the alpha side chain and are cardiovascular agents useful, for example, in the treatment of thrombotic disease and in the preparation of radiolabelled analogs. These compounds have the structural formula

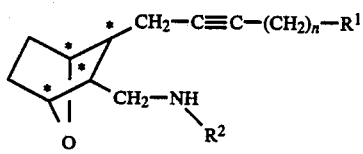

including all stereoisomers thereof, wherein n is 1 to 5; $R^1$ is $CO_2H$, $CO_2$ lower alkyl or

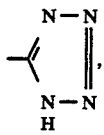

$R^2$ is

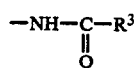

(wherein $R^3$ is lower alkyl, aralkyl, —NH-alkyl or NH-aryl); or

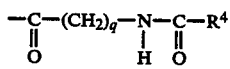

wherein q is 1 to 12; and $R^4$ is lower alkyl, lower alkenyl, lower alkynyl, aryl, arylalkyl, lower alkoxy, arylalkyloxy, aryloxy, amino, alkylamino, arylalkylamino, arylamino, lower alkyl-S—, aryl-S—, arylalkyl-S—,

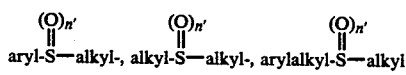

(wherein n' is 0, 1 or 2), alkylaminoalkyl, arylaminoalkyl, arylalkylaminoalkyl, alkoxyalkyl, aryloxyalkyl or arylalkoxyalkyl.

Thus, the compounds of formula I cover the following types of compounds:

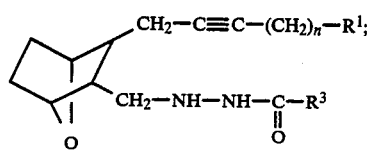

and

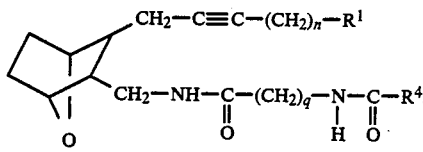

The term "lower alkyl" or "alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term $(CH_2)_n$ includes straight or branched chain radicals having from 1 to 5 carbons in the normal chain and may contain one or more lower alkyl and/or halogen substituents. Examples of $(CH_2)_n$ groups include $CH_2$,

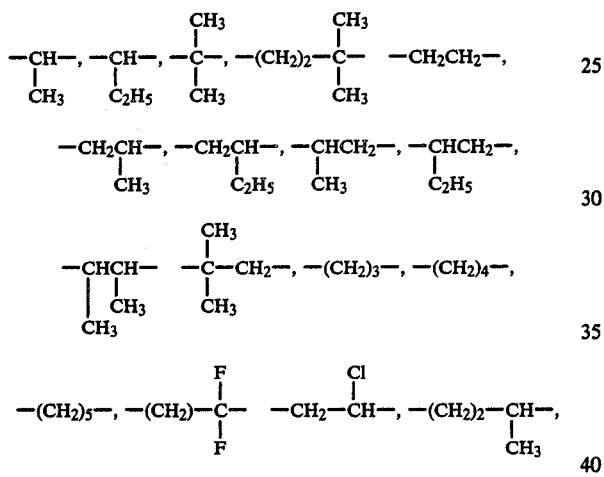

and the like.

The term $(CH_2)_q$ includes straight or branched chain radicals having from 1 to 12 carbons in the normal chain and includes any of the above examples of $(CH_2)_n$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

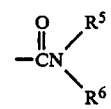

wherein $R^5$ and $R^6$ are independently hydrogen, lower alkyl or aryl.

The term "halogen" or "halo" as used herein refers to chlorine, bromine, fluorine, iodine and $CF_3$, with chlorine or fluorine being preferred.

Preferred are those compounds of formula I wherein n is 1 to 4, $R^1$ is $CO_2H$, $R^2$ is

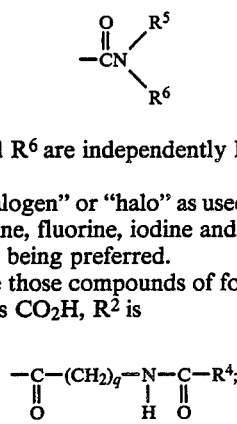

$(CH_2)_q$ is $—CH_2—$ and $R^4$ is lower alkyl such as pentyl, hexyl, or heptyl, or lower alkoxy such as pentoxy, lower alkylamino, such as pentylamino or arylthioalkyl, such as phenylthiomethyl.

The compounds of formula I of the invention may be prepared according to the following reaction sequence and as described below.

A. Where $R^2$ is $—\underset{\underset{O}{\|}}{C}—(CH_2)_q—\underset{H}{N}—\underset{\underset{O}{\|}}{C}—R^4$, $R^4 \neq NH_2$, and $R^1$ is COO alkyl or COOH

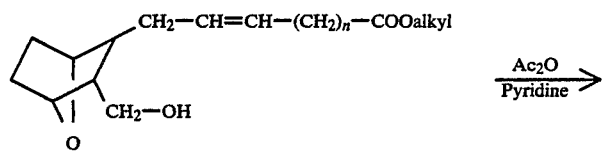

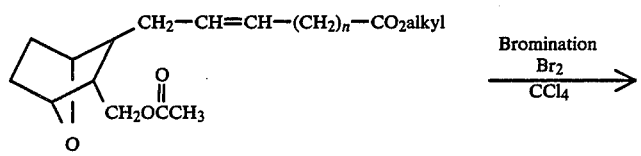

-continued

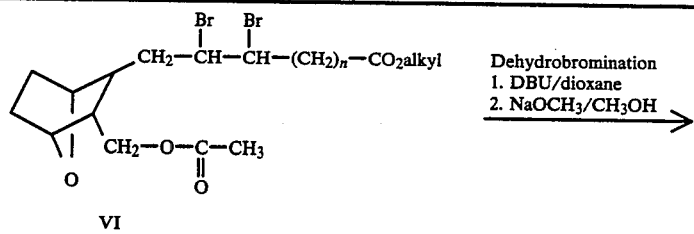

VI

Dehydrobromination
1. DBU/dioxane
2. NaOCH$_3$/CH$_3$OH →

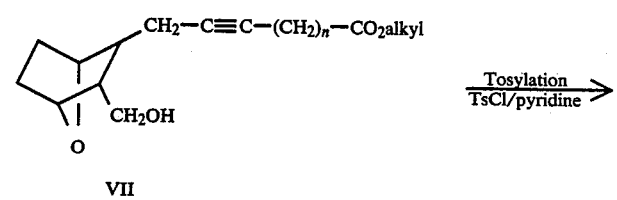

VII

Tosylation
TsCl/pyridine →

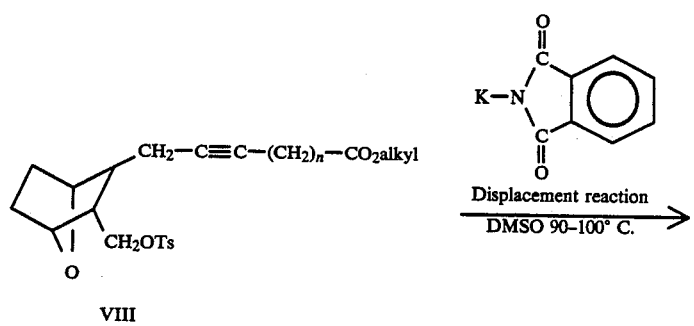

VIII

Displacement reaction
DMSO 90–100° C. →

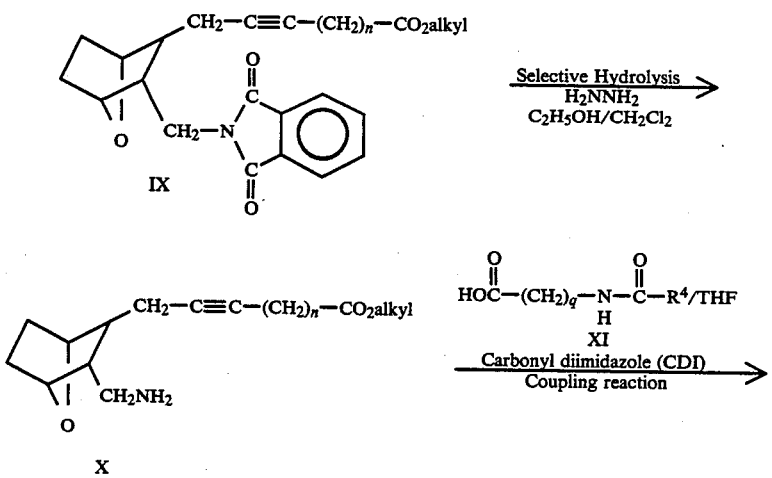

IX

Selective Hydrolysis
H$_2$NNH$_2$
C$_2$H$_5$OH/CH$_2$Cl$_2$ →

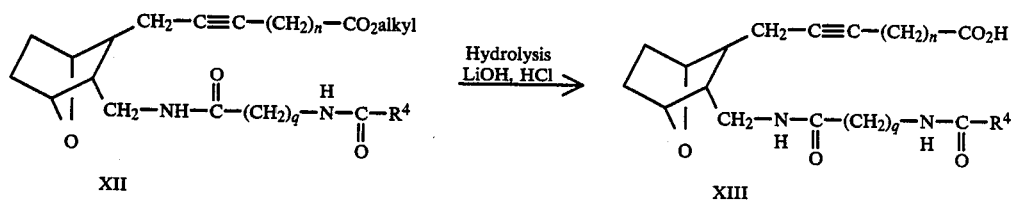

X $$HOC-(CH_2)_q-N-C-R^4/THF$$
$$\quad\;\, H$$
XI

Carbonyl diimidazole (CDI)
Coupling reaction →

XII

Hydrolysis
LiOH, HCl →

XIII

A′. Where R$^2$ is $-\underset{\underset{O}{\|}}{C}-(CH_2)_q-NH-\underset{\underset{O}{\|}}{C}-NH_2$

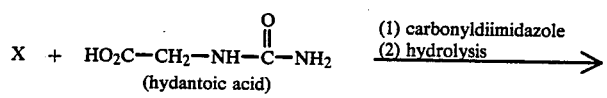

X + HO$_2$C—CH$_2$—NH—C(=O)—NH$_2$ 
(hydantoic acid)

(1) carbonyldiimidazole
(2) hydrolysis →

-continued

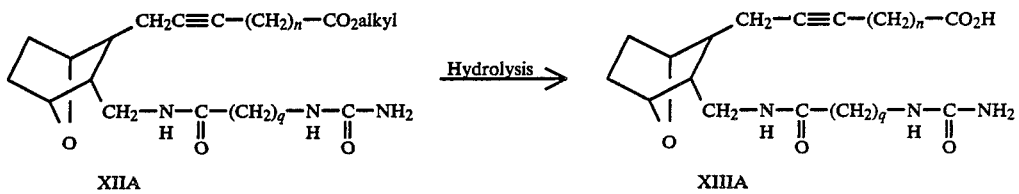

XIIA → Hydrolysis → XIIIA

A″. Where $R^2$ is $-\underset{\underset{O}{\|}}{C}-(CH_2)_q-NH-\underset{\underset{O}{\|}}{C}-R^4$

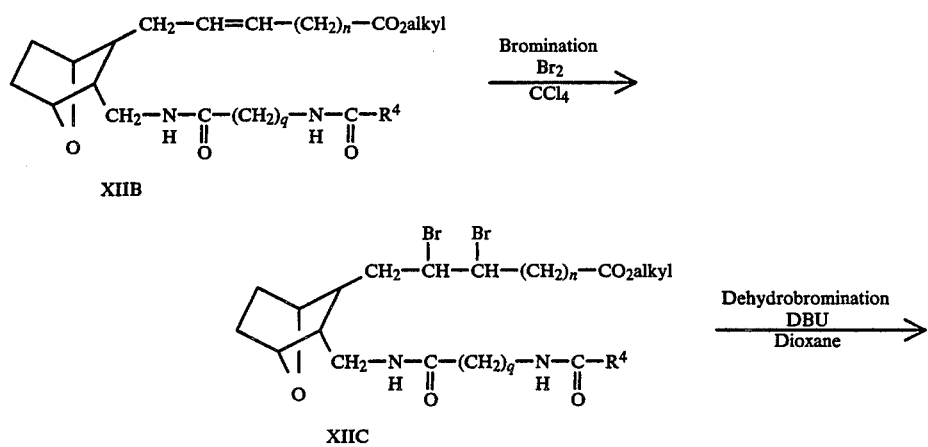

XIIB → Bromination $Br_2$/$CCl_4$ → XIIC → Dehydrobromination DBU/Dioxane →

XII → Hydrolysis LiOH, HCl → XIII

B. Where $R^2$ is $-NH-\underset{\underset{O}{\|}}{C}-R^3$ and $R^1$ is COOalkyl or COOH

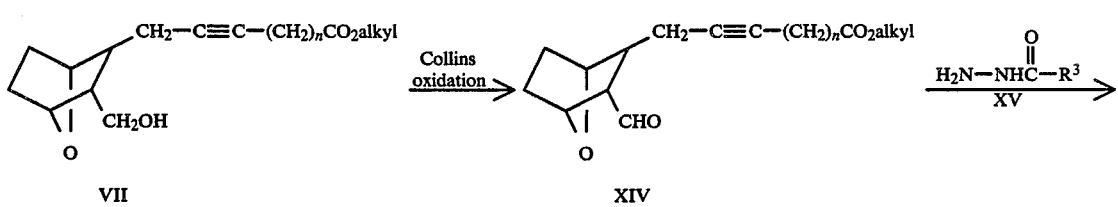

VII → Collins oxidation → XIV → $H_2N-NHC-R^3$ / XV →

(procedure as described in U.S. Pat. No. 4,416,896)

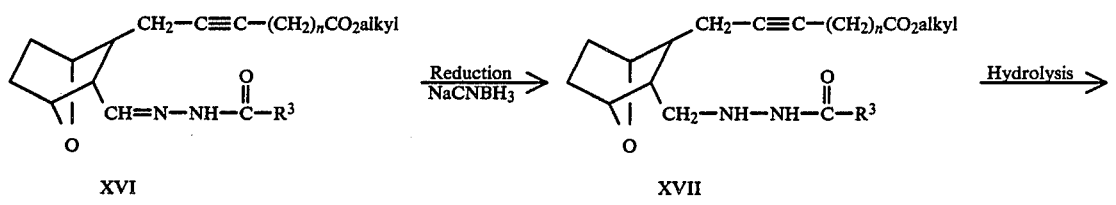

XVI → Reduction NaCNBH$_3$ → XVII → Hydrolysis →

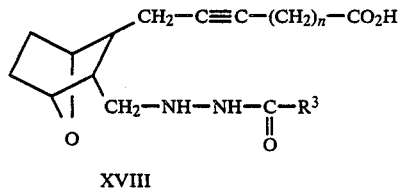

XVIII

-continued
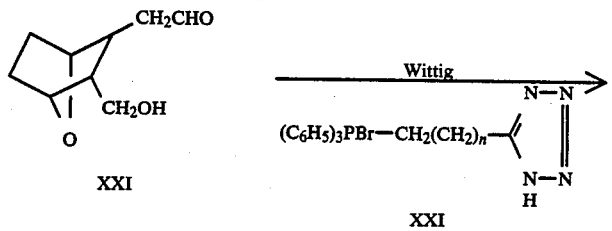
XXI
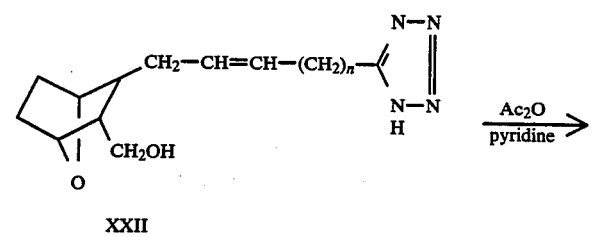
XXII
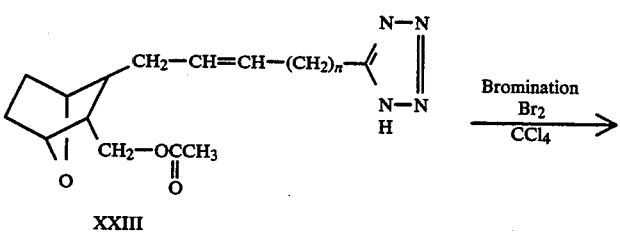
XXIII
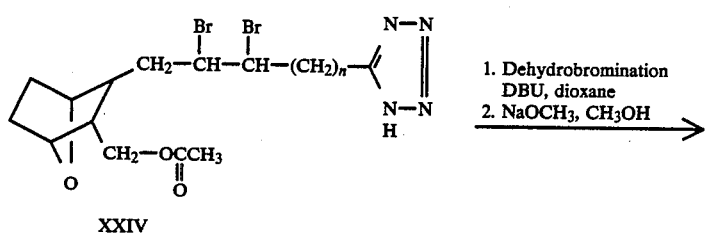
XXIV
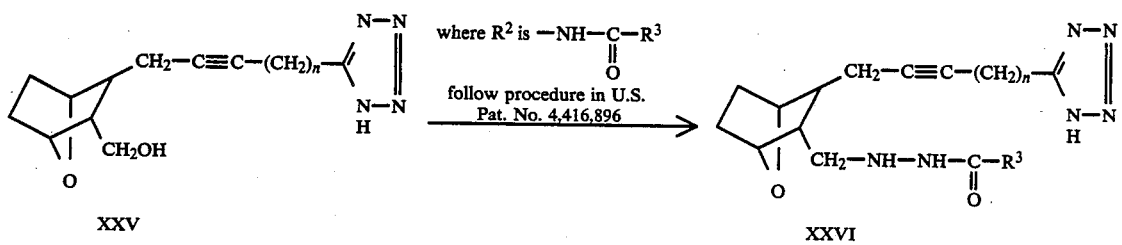
XXV → XXVI
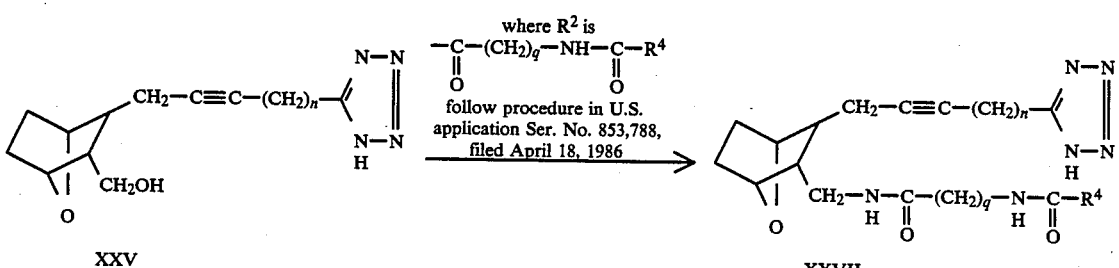
XXV → XXVII As seen in reaction sequence "A", compounds of the invention wherein $R^2$ is

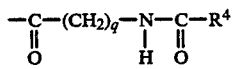

and $R^1$ is COOalkyl or COOH may be prepared by acylating the lower alkyl ester IV by reacting IV with, for example, acetic anhydride in the presence of pyridine to form V which is brominated by reaction with bromine in the presence of a chlorinated hydrocarbon solvent such as carbon tetrachloride at a temperature with the range of from about $-10°$ C. to about $20°$ C. to form the dibromide compound VI. Compound VI is then subjected to a dehydrobromination reaction by treating VI in solution with dioxane with 1,8-diazabicyclo[5.4.0]undec-7-ene (DBU) under an inert atmosphere such as argon, at a temperature of within the range of from about $70°$ C. to about $100°$ C. to form intermediate acetate which is subjected to methanolysis by treatment with catalytic base, for example NaOMe, in methanol to afford alcohol VII.

Alcohol VII is then tosylated by reacting VII with tosyl chloride in the presence of pyridine to form the corresponding tosylate VIII which is subjected to a displacement reaction by dissolving VIII in dimethylsulfoxide and heating to $90°$ to $100°$ C. in the presence of potassium phthalimide to form the phthalimide IX. The phthalimide IX is then made to undergo selective hydrolysis by dissolving IX in methylene chloride under an inert atmosphere such as argon and reacting with anhydrous hydrazine to form the amine X. The amine X is then subjected to a CDI coupling reaction by reacting X with acid XI

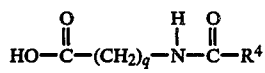

in the presence of an inert organic solvent such as tetrahydrofuran and carbonyl diimidazole under an inert atmosphere, such as argon, employing a molar ratio of X:XI of within the range of from about 1:1 to about 1:1.2, to form the amide ester compound XII

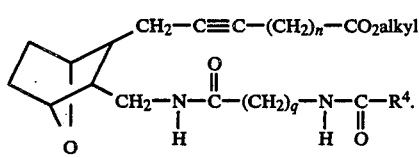

The ester XII is converted to the free acid, that is, to

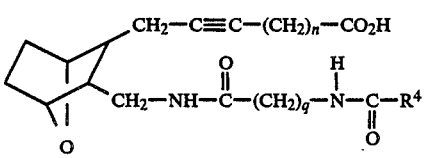

by treating the ester XII with a base, such as lithium hydroxide, sodium hydroxide or potassium hydroxide to form the corresponding alkali metal salt, followed by neutralization with an acid, such as dilute HCl or oxalic acid to form the acid XIII.

Referring now to reaction scheme "A''''", compounds of the invention wherein $R^2$ is

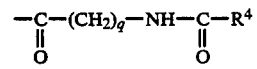

may alternatively be prepared by starting with the double amide XIIB (prepared as described in U.S. application Ser. No. 853,788, filed Apr. 18, 1986) which is brominated by reaction with bromine in the presence of a chlorinated solvent such as carbon tetrachloride at a temperature within the range of from about $-10°$ C. to about $20°$ C. to form the dibromide XIIC. Dibromide XIIC is then subjected to dehydrobromination by treating XIIC in solution with dioxane with DBU under an inert atmosphere such as argon, at a temperature within the range of from about $70°$ C. to about $100°$ C. to form ester XII which may be hydrolyzed to acid XIII.

In reaction sequence B, compounds of the invention wherein $R^2$ is

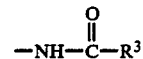

and $R^1$ is COOalkyl or COOH, that is XVII or XVIII, may be prepared from hydroxymethyl compound VII as outlined in U.S. Pat. No. 4,416,896, that is compound VII is subjected to a Collins oxidation, for example, by reacting VII with chromium trioxide in pyridine to form aldehyde XIV which is reacted with a hydrazine derivative XV to form compound XVI, employing a molar ratio of VII:XV of within the range of from about 0.8:1 to about 1:1 in a protic solvent such as methanol or ethanol. Compound XVI is then reduced, such as by reacting XVI with a reducing agent such as $NaBH_3CN$ or $NaBH_4$ in the presence of acetic acid or hydrogen with palladium on carbon as a catalyst to form ester compound XVII. Ester compound XVII may then by hydrolyzed to the corresponding acid XVIII by treating XVII with a base such as lithium hydroxide, followed by neutralization with an acid, such as dilute hydrochloric acid or oxalic acid.

In reaction sequence "A'''" compounds of the invention wherein $R^4$ is $NH_2$, that is XIIA and XIIIA

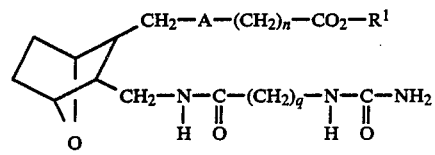

XIIA—wherein $R^1$ is alkyl
XIIIA—wherein $R^1$ is H may be prepared by reacting amine X with hydantoic acid in the presence of carbonyldiimidazole and then hydrolyzing the resulting product to form XIIA.

Compounds of the invention wherein $R^1$ is tetrazole

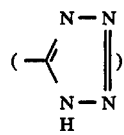

and $R^2$ is

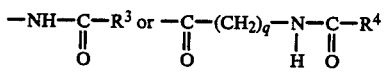

are prepared as described in reaction sequence "C" wherein alcohol XX

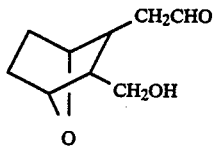     XX (prepared as described in U.S. Pat. No. 4,143,054) is reacted with a Wittig reagent of the structure XXI

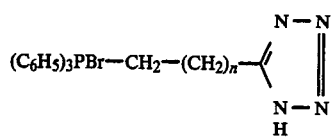     XXI in the presence of a base, such as potassium t-butoxide or sodium hydride-dimethyl sulfoxide employing a molar ratio of XX:XXI of within the range of from about 1:1 to about 0.2:1 to form the hydroxymethyl compound XXII

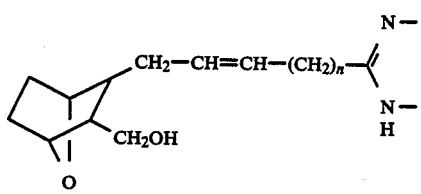     XXII which may then be employed in reaction sequences "A", "A'" and "B" in place of compounds IV and X to form compounds of the invention XXVI where $R^2$ is

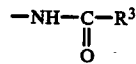

or XXVII where $R^2$ is

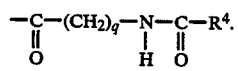

The starting acid XI

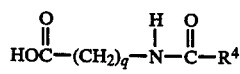     XI may be prepared by reacting the amino acid A

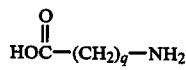     A with acid chloride B

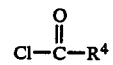     B in the presence of a strong base such as NaOH and water.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

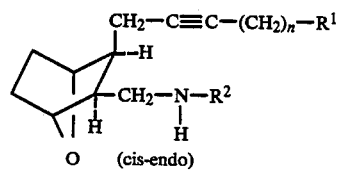     Ia (cis-endo)

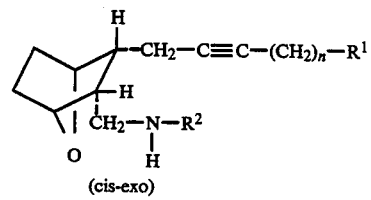     Ib (cis-exo)

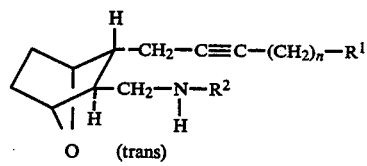     Ic (trans)

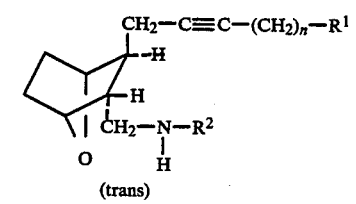     Id (trans)

The nucleus in each of the compounds of the invention is depicted as

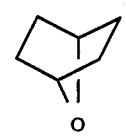

for matter of convenience; it will also be appreciated that the nucleus in the compounds of the invention may be depicted as

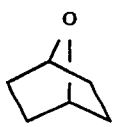

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

In addition, the compounds of the invention are useful in the preparation of radiolabelled analogs useful in testing the compounds of the invention.

The compounds of the invention can be administered orally or parenterally to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α,3α,4β]]-7-[3-[[[[(1-Oxoheptyl)amino]acetyl-]amino]methyl]-7-oxabicyclo[2.2.1]hept-2-yl]-5-heptynoic acid, methyl ester To a 0° C. solution of 1.22 g (2.82 mmol) of [1S-[1β,2α(5Z),3α,4β]]-7-[3-[[[[(1-oxoheptyl)amino]acetyl-]amino]methyl]-7-oxabicyclo[2.2.1]hept-2-yl]-5-heptenoic acid, methyl ester (prepared as described in U.S. patent application Ser. No. 853,788, filed May 18, 1986) in 10 ml of CCl₄ was added 0.15 ml (2.93 mmol) of bromine over approximately 2 minutes. It appeared that some compound had oiled out so 2.0 ml of CHCl₃ was added. The ice bath was removed and the reaction mixture was stirred at room temperature for 2.5 hours. The reaction mixture was diluted with 30 ml of CH₂Cl₂ and washed with 30 ml of saturated Na₂S₂O₅ solution. Addition of 10 ml H₂O aided in phase separation. The aqueous layer was extracted with 30 ml CH₂Cl₂ and then with 30 ml EtOAc. The combined organic extracts were dried over MgSO₄, filtered and concentrated in vacuo to give 1.64 g of crude dibromide.

The crude dibromide was dissolved in 12 ml of dioxane (Burdick and Jackson) and then 4.0 ml of 1,8-diazabicyclo[5.4.0]undec-7-ene (DBU) (26.8 mmol) was added. The flask was covered with foil and then heated to 95° C. under Ar for 20 hours. The cooled reaction mixture was partitioned between 100 ml EtOAc, 30 ml 1N HCl and 60 ml of saturated NaCl solution. The aqueous layer was extracted with 2×100 ml EtOAc. The combined EtOAc layers were washed with 50 ml H₂O, dried over MgSO₄, filtered and concentrated in vacuo. The residue was dissolved in minimal CH₃OH and treated with excess ethereal CH₂N₂. Purification was effected by flash chromatography on 45 g silica using 4% MeOH/CH₂Cl₂ to afford 0.62 (51%) of pure title compound along with 0.25 g (20%) of impure title compound.

EXAMPLE 2

[1S-[1β,2α,3α,4β]]-7-[3-[[[[(1-Oxoheptyl)amino]acetyl-]amino]methyl]-7-oxabicyclo[2.2.1]hept-2-yl]-5-heptynoic acid The two samples of title compound of Example 1 were hydrolyzed under standard conditions (10:2:1, THF/1N LiOH/H₂O) to afford a total of 640 mg of title acid. m.p. 125°–128° C., $[\alpha]^D = -6.5$ (C=1.05, MeOH).

Anal Calcd for $C_{23}H_{36}N_2O_5$: C, 65.69; H, 8.63; N, 6.66. Found: C, 65.56; H, 8.55; N, 6.76.

EXAMPLE 3

[1R-[1β,2α,3α,4β]]-7-[3-[[[[(1-Oxoheptyl)amino]acetyl-]amino]methyl]-7-oxabicyclo[2.2.1]hept-2-yl]-5-heptynoic acid, methyl ester

A.

[1R-[1α,2β(5Z),3β,4α]]-7-[[3-(Acetyloxymethyl)]-7-oxabicyclo[2.2.1]hept-2-yl]-5-heptenoic acid, methyl ester To a stirred solution of 2.0 g (7.5 mmol) of [1S-[1α,2β(5Z),3β,4α]]-7-[3-(hydroxymethyl)]-7-oxabicyclo[2.2.1]hept-2-yl]-5-heptenoic acid, methyl ester and 1.0 ml (12.4 mmol) of pyridine in 50 ml of CH₂Cl₂ was added 1.0 ml (10.6 mmol) of acetic anhydride. This solution was stirred at room temperature for 16 hours and then partitioned between 50 ml each of ether and 0.5N HCl. The aqueous layer was extracted with ether. The combined ether layers were back-extracted with 50 ml of H₂O, dried over MgSO₄, filtered and concentrated in vacuo to afford 2.3 g of title compound.

B.

[1R-[1α,2β,3β,4α]]-7-[[3-(Acetyloxymethyl)]-7-oxabicyclo[2.2.1]hept-2-yl]-5,6-dibromoheptanoic acid, methyl ester Without further purification, Part A compound was dissolved in 25 ml CCl₄, cooled to −20° C. and then 0.38 ml (7.4 mmol) of bromine was added dropwise. A large amount of yellow precipitate formed, as a result 3 ml CH₂Cl₂ was added. The −20° C. bath was exchanged for an ice-bath. After an additional 80 minutes, the reaction mixture was partitioned between 50 ml each CH₂Cl₂ and Na₂S₂O₅. The aqueous layer was extracted with 40 ml CH₂Cl₂. The combined organic layers were dried over MgSO₄, filtered and concentrated in vacuo to afford 3.6 g of a colorless oil. Purification was effected by chromatography on 72 g of silica gel using 1:1 hexane-ether as eluant to afford 1.89 g (54%) of title compound as a single diastereomer.

C.

[1R-[1α,2β,3β,4α]]-7-[[3-(Acetyloxymethyl)]-7-oxabicyclo[2.2.1]hept-2-yl]-5-heptynoic acid, methyl ester The crude Part B dibromide (1.50 g) was dissolved in 12 ml of dioxane (Burdick and Jackson) and then 4.0 ml of 1,8-diazabicyclo[5.4.0]undec-7-ene (DBU) (26.8 mmol) was added. The flask was covered with foil and then heated to 95° C. under Ar for 20 hours. The cooled reaction mixture was partitioned between 100 ml EtOAc, 30 ml 1N HCl, and 60 ml of saturated NaCl solution. The aqueous layer was extracted with 2×100 ml EtOAc. The combined EtOAc layers were washed with 50 ml $H_2O$, dried over $MgSO_4$, filtered and concentrated in vacuo. The residue was dissolved in minimal $CH_3OH$ and treated with excess ethereal $CH_2N_2$. Purification was effected by flash chromatography on 45 g silica using 4% $MeOH/CH_2Cl_2$ to afford 0.98 g (99%) of title acetylenic acetate compound.

D.

[1R-[1β,2α,3α,4β]]-7-[3-(hydroxymethyl)-7-oxabicyclo[2.2.1]hept-2-yl]-5-heptynoic acid, methyl ester The resulting Part C acetylenic acetate (0.98 g) was dissolved in 25 ml of methanol and treated with 0.1 g NaOMe. After stirring at room temperature for 2 hours, the reaction was complete. The mixture was neutralized by the addition of 2.5 ml of 1N HCl and then concentrated in vacuo. The residue was partitioned between 50 ml each half-saturated NaCl and EtOAc. The aqueous layer was extracted with 50 ml EtOAc. Combined organic layers were dried over $MgSO_4$, filtered and concentrated in vacuo to afford 0.8 g (94% overall from Part B compound) of title alcohol.

E.

[1R-[1β,2α(5Z),3α,4β]]-7-[3-[[[[(1-Oxoheptyl)amino]acetyl]amino]methyl]-7-oxabicyclo[2.2.1]hept-2-yl]-5-heptynoic acid, methyl ester (1)
[1R-[1β,2α(5Z),3α,4β]]-7-[3-(Tosyloxymethyl)-7-oxabicyclo[2.2.1]hept-2-yl]-5-heptynoic acid, methyl ester A solution of 0.8 (3.0 mmol) of Part D alcohol in 7.0 ml of pyridine and 8.0 ml of $CH_2Cl_2$ was cooled to 0° C. followed by the addition of 1.24 g (6.5 mmol) of tosyl chloride. The reaction mixture was allowed to warm to room temperature and stirred overnight. Reaction mixture was then poured into ice-water and stirred vigorously for 30 minutes. The products were extracted with EtOAc (100 ml×3). The combined EtOAc layers were washed with 3N-HCl (100 ml), $H_2O$ (100 ml) and dried over $MgSO_4$. Filtration and evaporation of solvent gave 1.26 g (100%) of crude tosylate which was used without purification.

(2)
[1R-[1β,2α(5Z),3α,4β]]-7-[(3-(Aminomethyl)-7-oxabicyclo[2.2.1]hept-2-yl]-5-heptynoic acid, methyl ester The title E(1) tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title E(1) tosylate (1.24 g, 2.95 mmol) and purified potassium phthalimide (1.1 g, 5.95 mmol, 2.0 equiv.) in dimethylsulfoxide (10.5 ml, Burdick and Jackson) were heated at 90°–100° C. for 3 hours (checked by TLC $Et_2O$-pet ether 2:1, no tosylate remaining). After cooling to room temperature, water (13 ml) was added. Material began precipitating. The mixture was poured into ice water (~50 ml) and stirred for 30 minutes. The straw colored solid was harvested by filtration and washed with more water. The solid was dissolved in warm ethyl acetate (50 ml), washed with water (2×25 ml), dried ($MgSO_4$), filtered and freed of solvent in vacuo. The remaining solid was recrystallized from isopropyl ether —EtOAc to give corresponding phthalimide, 830 mg (69%).

The above phthalimide (750 mg, 1.84 mmol) was dissolved in distilled $CH_2Cl_2$ (3.5 ml) and distilled ethanol (15 ml) in an argon atmosphere. Anhydrous hydrazine (0.12 ml, 3.94 mmol) was added. The mixture was stirred at room temperature. After 8 hours an additional 0.1 ml of hydrazine was added and the mixture was stirred an additional 15 hours at room temperature. A white solid was removed by filtration and washed with more $CH_2Cl_2$. The filtrate was taken to dryness in vacuo (on the pump at end). Residue triturated with cold 1.0N HCl solution (2×12 ml) The acidic solution was washed with ether (2×10 ml) and then basified with solid $K_2CO_3$. The amine was extracted into EtOAc (4×25 ml), dried ($MgSO_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (260 g, 53%). NMR spectra and TLC indicated some minor impurities. The material was used without further purification.

(3)[1R-[1β,2α(5Z),3α,4β]]-7-[3-[[[[(1-Oxoheptyl)amino]acetyl]amino]methyl]-7-oxabicyclo[2.2.1]hept-2-yl]-5-heptynoic acid, methyl ester 2-(Heptanoylamino)acetic acid prepared as described in U.S. application Ser. No. 853,788, filed, Apr. 18, 1986, (290 mg, 1.55 mmol) was dissolved in distilled THF (6 ml) in an argon atmosphere. After cooling in an ice bath carbonyldiimidazole (CDI) (270 mg, 1.66 mmol) was added. The mixture was stirred cold for 30 min and then at room temperature for 2 hours. The solution was cooled to 0° C. and a solution of Part C amine (260 mg, 1.0 mmol) in THF (2 ml) was added. The mixture was left stirring overnight at room temperature. The reaction mixture was partitioned between 25 ml 1N HCl and 35 ml EtOAc. The aqueous layer was extracted with 25 ml EtOAc, combined organic layers washed with 15 ml $H_2O$, dried ($MgSO_4$) and freed of solvent in vacuo leaving a viscous oil. The oil was chromatographed on silica gel (27 g, Baker for flash chromatography), eluting with 4% MeOH in $CH_2Cl_2$ to give title compound as an oil (320 mg, 76%).

EXAMPLE 4

[1R-[1β,2α(5Z),3α,4β]]-7-[3-[[[[(1-Oxoheptyl-
)amino]acetyl]amino]methyl]-7-oxabicyclo[2.2.1]hept-
2-yl]-5-heptynoic acid The Example 3 methyl ester (310 mg, 0.7 mmol) was dissolved in distilled THF (10 ml) and water (1 ml) in an argon atmosphere. 1N LiOH solution (2.0 ml) was added and the mixture was stirred at room temperature for 8 hours. After acidification to pH=2 with 1N HCl, solid KCl and 10 ml EtOAc were added and the layers were separated. The aqueous layer was reextracted with CHCl$_3$ (3×25 ml). The combined organic layers were dried (MgSO$_4$), and freed of solvent in vacuo leaving a white solid. This was recrystallized from ~3 ml EtOAc to give title acid, 180 mg, 60%.

EXAMPLE 5

[1S-[1β,2α,3α,4β]]-7-[3-[[[[(1-Oxoheptyl)amino]acetyl-
]amino]methyl]-7-oxabicyclo[2.2.1]hept-2-yl]-1-(1H-tet-
razol-5-yl)-4-hexyne

A.

[1S-[1β,2α(Z),3α,4β]]-6-[3-Hydroxymethyl-7-oxabicy-
clo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide title A compound.

B.

[1S-[1β,2α(5Z),3α,4β]]-6-[3-[[[[(1-Oxoheptyl-
)amino]acetyl]amino]methyl]-7-oxabicyclo[2.2.1]hept-
2-yl]-1-(1H-tetrazol-5-yl)-4-hexyne Following the procedure of Example 3 except substituting the Part A compound for the Example 3 Part D hydroxymethyl compound used in Example 3 Part E(1), the title compound is obtained.

EXAMPLE 6

[1S-[1α,2β,3β,4α]]-7-[3-[[2-[(Phenylamino)carbonyl]-
hydrazino]methyl]-7-oxabicyclo[2.2.1]hept-2-yl]-5-hep-
tynoic acid, methyl ester

A.

[1S-[1β,2α,3α,4β]]-7-[3-Formyl-7-oxabicyclo[2.2.1-
]hept-2-yl]-5-heptynoic acid, methyl ester Following the procedure as outlined in Example 2 Part A of U.S. Pat. No. 4,416,896 except substituting [1S-[1β,2α,3α,4β]]-7-[3-(hydroxymethyl)-7-oxabicy-
clo[2.2.1]hept-2-yl]-5-heptynoic acid, methyl ester for [1β,2α,3α,4β]]-7-[3-(hydroxymethyl)-7-oxabicy-
clo[2.2.1]hept-2-yl]-5-heptenoic acid, methyl ester, the title aldehyde was obtained.

B.

[1S-[1α,2β,3β,4α]]-7-[3-[[2-[(Phenylamino)carbonyl]-
hydrazono]methyl]-7-oxabicyclo[2.2.1]hept-2-yl]-5-
heptynoic acid, methyl ester Part A chiral aldehyde (1.99 g, 7.4 mmol) was dissolved in 22 ml EtOH in an argon atmosphere. 4-Phenylsemicarbazide (1.23 g, 8.1 mmol, recrystallized from water) (250 ml) was added. The mixture was stirred at room temperature for 24 hours. The solvent was removed in vacuo. The residue was chromatographed on 45 g of silica gel (Baker, for flash chromatography), eluting with 1% CH$_3$OH/CH$_2$Cl$_2$ to give 1.86 g (63%) of the title compound as a mixture of syn and anti isomers.

C.

[1S-[1α,2β,3β,4α]]-7-[3-[[2-[(Phenylamino)carbonyl]-
hydrazino]methyl]-7-oxabicyclo[2.2.1]hept-2-yl]-5-hep-
tynoic acid, methyl ester Part B compound (1.86 g, 4.67 mmol) was dissolved in MeOH (46 ml) in an argon atmosphere. Sodium cyanoborohydride (0.34 g, 5.40 mmol) was added followed by dropwise addition of glacial acetic acid (12 ml) over a period of 3 minutes. After stirring at room temperature for 240 minutes, an additional 75 mg NaCNBH$_3$ was added. After stirring an additional 90 minutes, the reaction mixture was diluted with 1N HCl until pH=1.0 and then stirred vigorously for 30 minutes. The reaction mixture was diluted with 150 ml H$_2$O and solid NaHCO$_3$ was added portionwise to pH 7–8. The product was extracted into EtOAc (3×200 ml). The combined extracts were dried (MgSO$_4$), filtered and freed of solvent in vacuo. The crude product was recrystallized from EtOH, EtOAc, isopropyl ether to give 1.39 g (74%) title compound, m.p. 158°–158.5° C.

EXAMPLE 7

[1S-[1α,2β,3β,4α]]-7-[3-[[2-[(Phenylamino)carbonyl]-
hydrazino]methyl]-7-oxabicyclo[2.2.1]hept-2-yl]-5-hep-
tynoic acid The Example 6 methyl ester (1.63 g, 4.06 mmol) was dissolved in a mixture of distilled THF (40 ml) and water (8 ml) which had been purged with argon. A solution of argon purged 1N LiOH (4 ml) was added and the mixture was stirred at room temperature 5 hours. The reaction mixture was partitioned between 150 ml each of saturated aqueous NaCl and EtOAc. The aqueous layer was acidified to pH=3.5 with 1N HCl. The aqueous layer was then extracted with EtOAc (2×150 ml). The combined extracts were dried (MgSO$_4$), and freed of solvent in vacuo.

Crude product was chromatographed on 50 g silica gel using 4% CH$_3$OH/CH$_2$Cl$_2$ as eluant to afford 1.00 g title compound.

Anal Calcd for C$_{21}$H$_{27}$O$_4$N$_3$: C, 65.43; H, 7.06; N, 10.90. Found: C, 65.06; H, 6.99; N, 10.75.

TLC: silica gel, 6% MeOH in CH$_3$OH/CH$_2$Cl$_2$, UV+PMA $R_f$=0.25

[α]$_D$= +0.85 (c=0.99, CHCl$_3$).

EXAMPLE 8

[1S-[1α,2β,3β,4α]]-7-[3-[[2-[(Phenylamino)carbonyl]-hydrazino]methyl]-7-oxabicyclo[2.2.1]hept-2-yl]-1-(1H-tetrazol-5-yl)-4-hexyne

Following the procedure of Example 6 except substituting the Example 5 Part A hydroxymethyl compound for the hydroxymethyl compound employed in Example 6 Part A, the title compound is obtained.

EXAMPLES 9 TO 57

Following the procedures outlined in the specification and described in the above working Examples, the following compounds may be prepared.

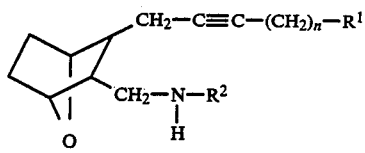

| Ex. No. | $(CH_2)_n$ | $R^1$ | $(CH_2)_q$ | $R^2$ is $-\underset{\underset{O}{\parallel}}{C}-(CH_2)_q-\underset{\underset{H}{\mid}}{N}-\underset{\underset{O}{\parallel}}{C}-R^4$ <br> $R^4$ |
|---|---|---|---|---|
| 9. | $\underset{\underset{-CH-}{\mid}}{CH_3}$ | $CO_2H$ | $(CH_2)_7$ | $-CH_2-\underset{\underset{H}{\mid}}{C}=\underset{\underset{H}{\mid}}{C}-CH_3$ |
| 10. | $-\underset{\underset{CH_3}{\mid}}{\overset{\overset{CH_3}{\mid}}{C}}-$ | $CO_2H$ | $\underset{\underset{-CH-}{\mid}}{CH_3}$ | $OC_6H_5$ |
| 11. | $(CH_2)_4$ | $CO_2H$ | $-CH_2-$ | $C_6H_5$ |
| 12. | $\underset{\underset{-C-CH_2-}{\mid}}{\overset{CH_3 \quad CH_3}{\diagup}}$ | $CO_2H$ | $\underset{\underset{-CH_2-CH-}{}}{CH_3}$ | $CH_2C_6H_5$ |
| 13. | $\overset{CH_3 \quad CH_3}{\underset{-CH-CH}{\diagup}}$ | $CO_2H$ | $\overset{CH_3 \quad CH_3}{\underset{-CH_2-C-}{\diagup}}$ | $-(CH_2)_2C_6H_5$ |
| 14. | $\underset{\underset{F}{\mid}}{\overset{\overset{CH_3}{\mid}}{-C-CH_2-}}$ | ![tetrazole] N—N / \\ N—N H | $\underset{\underset{-CH_2-CH-CH_2-}{}}{CH_3}$ | $-C_6H_4-p-CH_3$ |
| 15. | $\underset{\underset{-CH-CH-}{}}{\overset{F \quad F}{\mid \quad \mid}}$ | $CO_2H$ | $-(CH_2)_3-$ | $-C_6H_4-p-OH$ |
| 16. | $\overset{F \quad F}{\underset{-C-CH_2-}{\diagup}}$ | $CO_2H$ | $\underset{\underset{-CH_2-CH-}{}}{C_2H_5}$ | $-OCH_2C_6H_5$ |
| 17. | $-(CH_2)_5-$ | tetrazole N—N / \\ N—N H | $\underset{\underset{H}{\mid}}{\overset{\overset{CH_3}{\mid}}{-CH_2-C-CH_2-}}$ | $-SC_2H_5$ |
| 18. | $\underset{\underset{-CH_2-CH-CH_2-}{}}{CH_3}$ | $CO_2C_4H_9$ | $\underset{\underset{CH_3}{\mid}}{\overset{\overset{CH_3}{\mid}}{-C-CH_2-}}$ | $-OC_6H_5$ |
| 19. | $\overset{CH_3 \quad CH_3}{\underset{-CH_2-C-}{\diagup}}$ | $CO_2H$ | $(CH_2)_2$ | $-NH_2$ |
| 20. | $CH_2$ | $CO_2H$ | $-CH_2-$ | $-NHCH_3$ |
| 21. | $(CH_2)_2$ | tetrazole N—N / \\ N—N H | $\underset{\underset{CH_3}{\mid}}{\overset{\overset{CH_3}{\mid}}{-CH_2-C-}}$ | $-NHC_6H_5$ |

-continued

[Structure: bicyclic skeleton with CH₂−C≡C−(CH₂)ₙ−R¹ and CH₂−N(H)−R² substituents, and O]

| # | | | | |
|---|---|---|---|---|
| 22. | (CH₂)₃ | CO₂H | −CH₂−CH(CH₃)−CH(CH₃)−CH₂− | −NCH₃(C₂H₅) |
| 23. | (CH₂)₄ | CO₂H | (CH₂)₂ | −N(CH₃)₂ |
| 24. | −CH₂CF₂− | [tetrazole N−N/N−NH ring with CH₃] | (CH₂)₃ | CH₃ |
| 25. | −CH₂C(CH₃)₂− | CO₂H | −CHF−CH₂− | −NH−CH₂−C₆H₅ |
| 26. | (CH₂)₅ | CO₂H | −CF₂−CH₂ | −(CH₂)₂CH=CHCH₃ |
| 27. | −CH(CH₃)−CHF− | CO₂H | (CH₂)₂ | C₆H₅ |
| 28. | (CH₂)₂ | [tetrazole ring] | CH₂ | −CH₂C₆H₅ |
| 29. | (CH₂)₃ | CO₂H | (CH₂)₃ | −SC₄H₉ |
| 30. | (CH₂)₄ | CO₂H | (CH₂)₈ | −SC₆H₅ |
| 31. | (CH₂)₅ | CO₂H | (CH₂)₁₀ | −NCH₃(C₆H₅) |
| 32. | CH₂ | CO₂H | (CH₂)₂ | CH₃ |
| 33. | (CH₂)₂ | CO₂H | (CH₂)₃ | CH₃ |
| 34. | (CH₂)₃ | [tetrazole ring] | (CH₂)₄ | −CH=CH−CH₃ |
| 35. | (CH₂)₄ | CO₂H | (CH₂)₅ | −C≡C−CH₃ |
| 36. | (CH₂)₅ | | (CH₂)₆ | −CH₂−C≡C−CH₃ |
| 37. | (CH₂)₃ | CO₂H | CH₂ | −CH₂−S(=O)−C₆H₅ |
| 38. | CH₂ | CO₂H | CH₂ | −CH₂−S(=O)−C₂H₅ |
| 39. | (CH₂)₃ | CO₂C₄H₉ | (CH₂)₂ | −CH₂−S(=O)−CH₂C₆H₅ |
| 40. | (CH₂)₃ | CO₂H | (CH₂)₃ | −CH₂−S−C₂H₅ |
| 41. | (CH₂)₃ | CO₂H | CH₂ | −CH₂−S−CH₂−C₆H₅ |
| 42. | (CH₂)₃ | CO₂H | CH₂ | −CH₂−O−CH₂−C₆H₅ |
| 43. | CH₂ | CO₂H | CH₂ | −CH₂−NH−CH₂C₆H₅ |

-continued

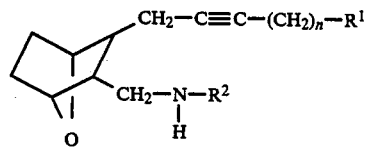

| 44. | (CH$_2$)$_3$ | 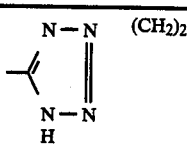 | (CH$_2$)$_2$ | —CH$_2$—S—C$_4$H$_9$ |

| Ex. No. | (CH$_2$)$_n$ | R$^1$ | R$^2$ is —NH—C(=O)—R$^3$<br>R$^3$ |
|---|---|---|---|
| 45. |  —CH— with CH$_3$ | CO$_2$H | C$_4$H$_9$ |
| 46. | 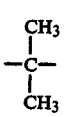 —C— with two CH$_3$ | CO$_2$H | —CH$_2$—C$_6$H$_5$ |
| 47. | (CH$_2$)$_4$ | CO$_2$H | —(CH$_2$)$_2$—C$_6$H$_5$ |
| 48. | 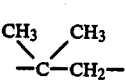 —C—CH$_2$— with two CH$_3$ | CO$_2$H | —NHCH$_2$C$_6$H$_5$ |
| 49. | 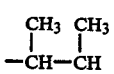 —CH—CH— with two CH$_3$ | CO$_2$H | —NH(CH$_2$)$_2$C$_6$H$_5$ |
| 50. | 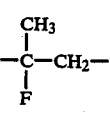 —C—CH$_2$— with CH$_3$ and F | 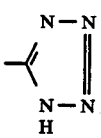 | —CH$_2$—C$_6$H$_4$—p-CH$_3$ |
| 51. |  —CH—CH— with two F | CO$_2$H | —CH$_2$—C$_6$H$_4$—p-OH |
| 52. | 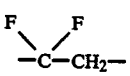 —C—CH$_2$— with two F | CO$_2$H | —NHC$_6$H$_5$ |
| 53. | —(CH$_2$)$_5$— | 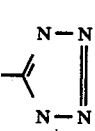 | —NC$_2$H$_5$<br>H |
| 54. | 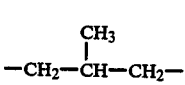 —CH$_2$—CH—CH$_2$— with CH$_3$ | CO$_2$C$_4$H$_9$ | 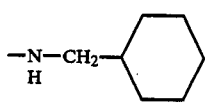 —N—CH$_2$—cyclohexyl<br>H |
| 55. | 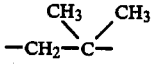 —CH$_2$—C— with two CH$_3$ | CO$_2$H | —NHC$_3$H$_7$ |
| 56. | CH$_2$ | CO$_2$H | —NHC$_6$H$_5$ |
| 57. | (CH$_2$)$_2$ | 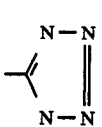 | —NHC$_5$H$_{11}$ |

What is claimed is:

1. A compound having the structure $$\text{[bicyclic structure with } CH_2-C{\equiv}C-(CH_2)_n-R^1 \text{ and } CH_2-N(H)-R^2 \text{ substituents, O in ring]}$$

including all stereoisomers thereof, wherein n is 1 to 5; $R^1$ is $CO_2H$, $CO_2$alkyl, or $$-\!\!\!\!{<}\!\!\begin{array}{c}N-N\\ \|\\ N-N\\ |\\ H\end{array};$$

$R^2$ is $$-NH-\underset{\underset{O}{\|}}{C}-R^3$$

wherein $R^3$ is lower alkyl, aralkyl, —NHalkyl or —N-Haryl, or $R^2$ is $$\underset{\underset{O}{\|}}{C}-(CH_2)_q-\underset{\underset{H}{|}}{N}-\underset{\underset{O}{\|}}{C}-R^4$$

wherein q is 1 to 12; and $R^4$ is lower alkyl, lower alkenyl, lower alkynyl, aryl, arylalkyl, lower alkoxy, arylalkloxy, aryloxy, amino, alkylamino, arylamino, arylalkylamino, lower alkyl—S—, aryl—S—, arylalkyl—S—, $$\underset{\underset{\|}{(O)_{n'}}}{\text{aryl-S—alkyl-,}} \quad \underset{\underset{\|}{(O)_{n'}}}{\text{alkyl-S—alkyl-,}} \quad \underset{\underset{\|}{(O)_{n'}}}{\text{arylalkyl-S—alkyl}}$$

(wherein n' is 0, 1 or 2), alkylaminoalkyl, arylaminoalkyl, arylalkylaminoalkyl, alkoxyalkyl or arylalkoxyalkyl, wherein aryl by itself or as part of another group is a monocyclic or bicyclic aromatic group containing 6 to 10 carbons in the ring portion.

2. The compound as defined in claim 1 wherein $R^2$ is $$\underset{\underset{O}{\|}}{C}-(CH_2)_q-\underset{\underset{H}{|}}{N}-\underset{\underset{O}{\|}}{C}-R^4$$

and $R^4$ is alkyl, alkoxy or arylthioalkyl.

3. The compound as defined in claim 1 wherein q is 1 to 4.

4. The compound as defined in claim 1 wherein n is 2 to 4.

5. The compound as defined in claim 1 wherein $R^2$ is $$-NH-\underset{\underset{O}{\|}}{C}-R^3.$$

6. The compound as defined in claim 1 wherein $R^1$ is $CO_2H$ or $$-\!\!\!\!{<}\!\!\begin{array}{c}N-N\\ \|\\ N-N\\ |\\ H\end{array}.$$

7. The compound as defined in claim 1 wherein $R^1$ is H.

8. The compound as defined in claim 1 wherein n is 2 to 4, $R^1$ is $CO_2H$, q is 1, $R^2$ is $$\underset{\underset{O}{\|}}{C}-(CH_2)_q-\underset{\underset{H}{|}}{N}-\underset{\underset{O}{\|}}{C}-R^4$$

and $R^4$ is alkyl, alkoxy or phenylthiomethyl.

9. The compound as defined in claim 1 having the name [1S-[1β,2α,3α,4β]]-7-[3-[[[[(1-oxoheptyl)amino]acetyl]amino]methyl]-7-oxabicyclo[2.2.1]hept-2-yl]-5-heptynoic acid or esters thereof, including all stereoisomers thereof.

10. The compound as defined in claim 1 having the name [1S-[1α,2β,3β,4α]]-7-[3-[[2-[(phenylamino)carbonyl]hydrazino]methyl]-7-oxabicyclo[2.2.1]hept-2-yl]-5-heptynoic acid.

11. A method of inhibiting platelet aggregation and/or bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting platelet aggregation and/or bronchoconstriction comprising an effective amount of a compound as defined in claim 1 or a pharmaceutically acceptable salt thereof, and a pharmaceutically acceptable carrier therefor.

14. A method of treating peripheral vascular diseases, which comprises topically or systemically administering to a mammalian host an effective amount of a compound as defined in claim 1 or a pharmaceutically acceptable salt thereof.

15. The method as defined in claim 14 wherein said compound is administered in an amount within the range of from about 1 to about 100 mg/kg.

16. A method for treating asthma in a mammalian species in need of such treatment, which comprises administering to a mammalian host an effective amount of a compound as defined in claim 1 or a pharmaceutically acceptable salt thereof.

* * * * *